United States Patent [19]
Levavi et al.

[11] Patent Number: 5,819,739
[45] Date of Patent: Oct. 13, 1998

[54] METHOD AND APPARATUS FOR CONTRAVENTION OF THE TRANSFER OF PATHOGENIC ORGANISMS BETWEEN PATIENTS VIA AN INFLATABLE CUFF USED FOR ARTERIAL BLOOD PRESSURE MEASUREMENT

[76] Inventors: Israel Levavi; Beatrice Levavi, both of 177 S. Gardner St., Los Angeles, Calif. 90036

[21] Appl. No.: 478,002

[22] Filed: Jun. 6, 1995

[51] Int. Cl.$^6$ ........................................................ A61B 5/00
[52] U.S. Cl. ........................... 128/686; 606/202; 428/906
[58] Field of Search .................... 128/677–680, 128/80–84, 645, 856; 606/201–207; 383/200, 41; 428/906

[56] References Cited

U.S. PATENT DOCUMENTS

| | | | |
|---|---|---|---|
| 4,871,046 | 10/1989 | Turner | 181/131 |
| 4,967,758 | 11/1990 | Masciarotte | 128/686 |
| 5,024,349 | 6/1991 | Haenni et al. | 221/46 |
| 5,228,448 | 7/1993 | Byrd | 128/686 |
| 5,513,643 | 5/1996 | Suite | 128/686 |

*Primary Examiner*—Robert L. Nasser, Jr.
*Attorney, Agent, or Firm*—A. M. Fernandez

[57] ABSTRACT

Barriers for contravention of the transfer of pathogenic organisms from one patient to another through an inflatable cuff comprised of a cuff and a bladder of a sphygmomanometer are supplied on a sterile roll of synthetic polymer segmented by transverse perforations so that each segment may be torn off and used as a barrier between a patient's skin and an inflatable cuff. The rolled segments may be tubular so that the barrier will be tubular in form in order to slip it over the patient's extremity. Each tubular barrier is perforated along one edge so that it can be torn longitudinally to convert the barrier from a tubular form to a rectangular form if needed. The tubular form is provided with ample circumference so that the excess can be gathered near the longitudinal perforations and folded over the longitudinal perforations in order to maintain the integrity of the barrier's function. Another form for barriers on a sterile roll of synthetic polymer is that of an envelope having cutouts on both sides as windows for fasteners of the cuff to permit one end to be fastened to the other end of the cuff wrapped around the patient's extremity. The reusable cuff inserted in such an envelope barrier is withdrawn from the envelope after use and discarded. A new sterile envelope is then taken from the roll for reuse of the inflatable cuff. Another effective measure for contravening the transfer of pathogenic organisms to a patient is to use a disposable inflatable cuff having a pocket for its bladder so that only the cuff is discarded, or having a cuff with its bladder formed as an integral part thereof.

2 Claims, 1 Drawing Sheet

METHOD AND APPARATUS FOR CONTRAVENTION OF THE TRANSFER OF PATHOGENIC ORGANISMS BETWEEN PATIENTS VIA AN INFLATABLE CUFF USED FOR ARTERIAL BLOOD PRESSURE MEASUREMENT

FIELD OF THE INVENTION

The invention relates to an inflatable cuff of a sphygmomanometer and more particularly to contravention of the transfer of pathogenic organisms between patients whose blood pressure measurements are taken sequentially with the same sphygmomanometer.

BACKGROUND ART

Arterial blood pressure measurement is required in the diagnosis and treatment of all manner of illness. It is indeed performed on any and all patients as part of the procedures for obtaining the so called "vital signs."

Currently arterial blood pressure is measured in only two ways. The most common is with the use of a sphygmomanometer illustrated in FIG. 1 composed of an inflatable bladder in a cuff 10 to compress an artery in a patient's extremity, an air pump 11 to inflate the bladder, a control valve 12 and an aneroid, mercury, or other manometer 13 in series with the inflatable bladder. The cuff (having a pocket for the bladder) is made from a fabric of woven synthetic polymer and is provided with a means 14 (Velcro or other fastener) for securing the cuff around the patient's extremity (arm, leg or other extremity). The cuff is wrapped around the extremity of the patient before the bladder is inflated to compress the artery. The cuff and bladder together are sometimes herein-after referred to as a unit called an "inflatable cuff," and from the context it will be clear when that is the case.

In use, the inflatable cuff is fastened in place around an extremity of the patient and inflated sufficiently to occlude an artery, most commonly the main artery in the patient's arm as shown in FIG. 1. Then while gradually deflating the bladder by operation of the valve 12, the systolic pressure indicated by the aneroid manometer 13 is recorded at the time flow of blood through the occluded artery is first heard through a stethoscope 15. Similarly, the diastolic pressure indicated by the manometer 13 is recorded at the time the sound of turbulent blood flow through the artery ceases.

The second method for measuring blood pressure is invasive and potentially hazardous, so it is normally not used except under carefully controlled sterile conditions which are normally maintained in emergency rooms, operating rooms, or critical care units where intra-arterial catheters are inserted in a patient's artery. Great care is always taken to maintain the sterility of the puncture site and anything connected to the catheter. This is because the potential for infection of the patient with disease via the catheter has been widely recognized and well described in the medical literature.

By contrast, the potential for infection from the inflatable cuff of a sphygmomanometer in direct contact with a patient's skin has been completely ignored, and the same inflatable cuff is used sequentially on many patients without sterilization, perhaps thousands of times over the life of the inflatable cuff, i.e., until there is need to replace the inflatable cuff because of simple wear.

The very nature of the fabric used for the cuff provides an ideal substrate for foreign matter which may harbor a variety of microscopic pathogens. The cuff covers a large surface area of skin which is frequently not intact. Inflatable cuffs are thus exposed over a large area to all manner of bodily fluids, e.g., blood, sweat, urine, fecal matter, etc., which harbor a dismaying variety of pathogenic organisms that the cuffs readily transfer to the next patient through skin contact. It is thus clear that there is a great potential for transfer of infectious diseases from one patient to another, particularly in emergency rooms where the condition, health and susceptibility of patients may not be fully known or understood by the medical staff at the time of emergency examination and/or treatment. One emergency patient examined may be suffering from a highly contagious disease, and the next in sequence may be highly susceptible to the disease.

STATEMENT OF THE INVENTION

The object of the invention is to contravene this potentially hazardous condition resulting from sequential use of the inflatable cuff of a sphygmomanometer by introducing effective measures for preventing the transfer of pathogenic organisms from one patient to the next due to sequential reuse of the sphygmomanometer for different patients.

In its broadest aspects, this object is achieved by an effective measure (method or apparatus) for contravention of the transfer of pathogenic organisms from one patient to the next, including sterilization of the inflatable cuff or sterilization of the cuff with the bladder removed using a sterilizing gas or other sterilizing means, taking into account the mechanical and chemical resistance of the inflatable cuff to the particular sterilization means employed.

Another effective measure is the provision of a sterile synthetic polymer barrier 16 between the inflatable cuff and the patient's skin as shown in FIG. 1, such as a supple synthetic polymer sheet, preferably in a tubular form that may be readily dispensed, such as from a roll of 200 or 300 tubular sheets connected by a row of closely and transversely spaced perforations between sheets. The sheets can then be readily separated from the roll in sequence by tearing through the perforations. This permits each tubular sheet separated from the roll to be used as a barrier to pathogenic organisms on a different patient by slipping the tubular sheet over the patient's extremity to the location where the inflatable cuff is to be placed for arterial blood pressure measurement. Alternatively, the barrier sheets in this tubular form, or any other form, may be dispensed from a box through an opening on top with the sheets either precut into separate barrier sheets or connected together by perforations and fan-folded for dispensing sequentially.

The tubular barrier sheets are selected to have an axial length sufficient to exceed the greatest width of any cuff to be applied or alternatively to have an axial length tailored for cuffs of different widths. In any case, each roll is selected to have tubular barrier sheets larger in circumference than the circumference of an inflatable cuff of a standard size for a child, an adult or a large adult for whom it is intended.

The barrier sheet of tubular form may be provided with a column of longitudinal perforations that are to be torn when it is applied to a patient having IV tubes or other appurtenances in place. The resulting rectangular barrier sheet can then be applied to the patient's extremity by simply going directly to the proximal part of the extremity and there wrapping it around the extremity without interfering with the IV tubes or other appurtenances. Alternatively, supple barrier sheets already of rectangular form may be provided either on a roll or in a box for such occasions.

The novel features that are considered characteristic of this invention are set forth with particularity in the appended claims. The invention will best be understood from the following description when read in connection with the accompanying drawings.

DETAILED DESCRIPTION OF THE INVENTION

Figure 1:
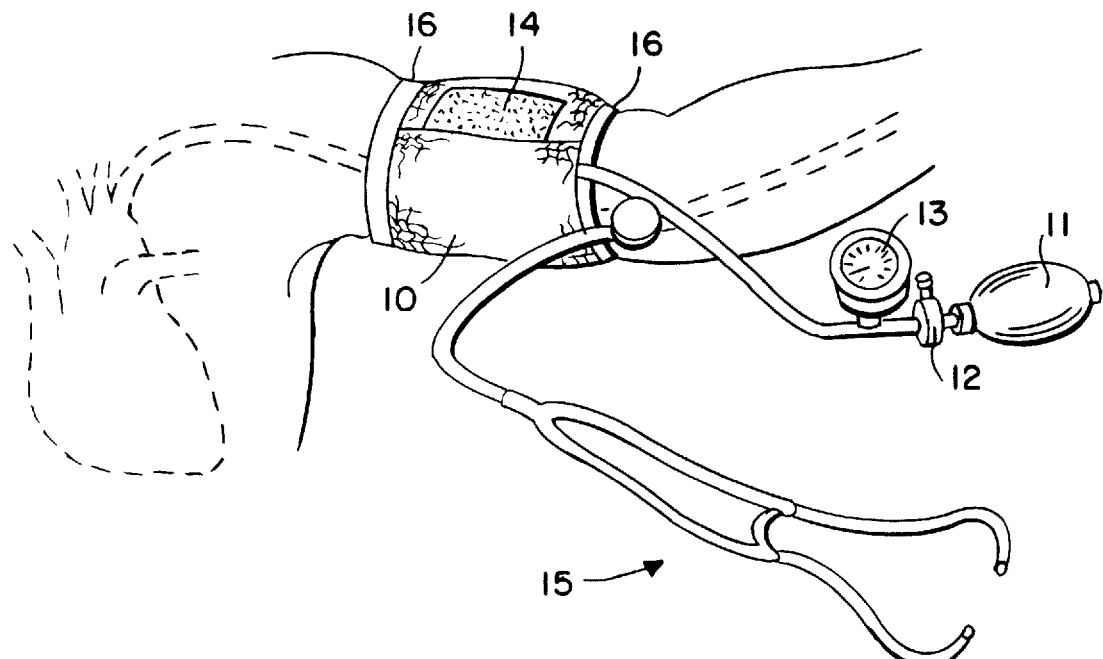
FIG. 1 illustrates a sphygmomanometer for measuring arterial blood pressure in a conventional manner using a stethoscope, but with a sterile disposable supple barrier placed between an inflatable cuff and a patient's skin in accordance with the present invention for preventing the transfer of pathogenic organisms from one patient to the next due to the use of the same inflatable cuff in examining many patients sequentially.
Figure 2:
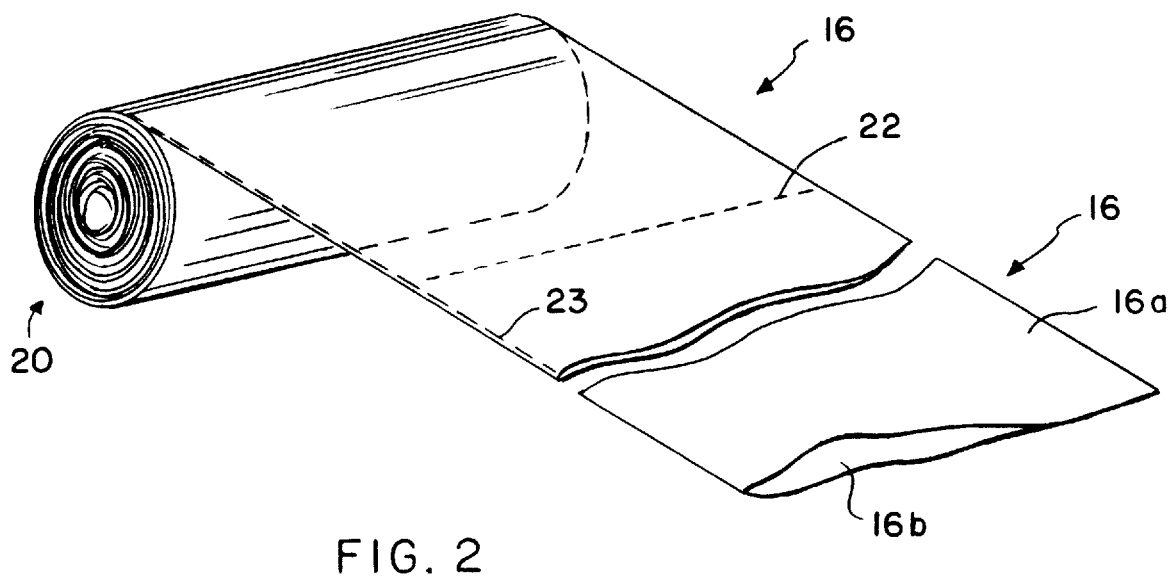
FIG. 2 illustrates an example of the present invention, namely sterile disposable supple barrier sheets dispensed from a roll in a tubular form so that a barrier can be slipped over the patient's extremity (e.g., arm as shown in FIG. 1) before applying the inflatable cuff. These tubular barrier sheets are provided with transverse perforations to facilitate tearing one barrier sheet at a time off the roll and longitudinal perforations so that the barrier sheet of tubular form may be torn along the longitudinal perforations to form a rectangular barrier sheet when a supple barrier sheet of tubular form cannot be used due to IV tubes or other appurtenances in place on the patient's extremity.

Referring to FIG. 2, a roll 20 provides 200 to 300 tubular barriers 16 (FIG. 1) of synthetic polymer, such as sheets of suitable thickness, connected by a row of perforations 22 between barriers so that they may be sequentially separated from the roll by tearing one barrier from the next through the perforations 22 which consist of closely and transversely spaced slits. Each barrier 16 coming off the roll 20 is essentially flat but is in fact tubular when the flat sides 16a and 16b connected on the edges are spread apart.

Each tubular barrier 16 torn off the roll 20 has an axial length about 2.5 cm more than the width of an inflatable cuff 10 (FIG. 1), which is typically 13½ cm for an adult cuff (about 17 cm for a large adult cuff and 10 cm for a child cuff) and a circumferential length sufficient to wrap over the patient's extremity (arm in FIG. 1) with enough overlap for securing the cuff with the Velcro fastener. Any excess length of the disposable barrier in circumference is gathered and folded over as the inflatable cuff 10 (FIG. 1) is snugly wrapped around the patient's extremity.

By providing an axial length of the barrier 16 of tubular form that is about 2.5 cm more than the cuff is wide, there is an excess of more than 1 cm of the tubular barrier 16 on each side of the inflatable cuff for contravention of the transfer of any pathogenic organisms from the previous patient to the present one. Thus, inflatable cuffs for sphygmomanometers can be used on many patients sequentially without risk of infecting one patient with the disease of a previous patient.

A feature of the tubular barrier 16 illustrated in FIG. 2 is a column 23 of perforations along one edge of both sides 16a and 16b so that if a rectangular barrier sheet is needed, a tubular barrier may be torn along its column 23 of perforations. This feature is useful when IV tubes and other appurtenances prevent a tubular barrier from being slipped over the patient's extremity, as noted hereinbefore. Having torn a tubular barrier along the column of perforations, the resulting rectangular barrier may be wrapped around the patient's extremity in its proper place before the inflatable cuff is applied for measuring arterial blood pressure without interfering with the IV tubes and other appurtenances. In order that the column 23 of perforations not compromise the barrier of tubular form if it is drawn over the patient's extremity as a sleeve, the excess of the tubular barrier is gathered near the column 23 of perforations so that those perforations will be included in the folded material, i.e., so that the perforations will overlay the unperforated side 16a or 16b.

From the foregoing disclosure, it is obvious that a roll of rectangular barrier sheets separated by rows of transverse perforations could be provided such that each rectangular sheet may be readily torn from the roll in sequence. That would be well within the scope of this invention and in fact may be preferred over tubular barriers in some situations even though IV tubes and other appurtenances have not yet been attached to the patient.

What is claimed is:

1. Barriers for contravention of the transfer of pathogenic organisms from one patient to another through a reusable inflatable cuff of a sphygmomanometer comprising a roll of supple barriers, said barriers being defined on a continuous web of supple barrier material of said roll by transverse rows of closely spaced perforations for allowing each barrier to be torn from said roll sequentially for placement between said reusable inflatable cuff and the skin of a patient's extremity, wherein each barrier on said roll is in a tubular form with open ends thereof being defined by said transverse rows of closely spaced perforations.

2. Barriers as defined in claim 1 wherein each barrier of tubular form includes a longitudinal column of closely spaced perforations close to one side thereof for said barrier of tubular form to be torn longitudinally to convert a barrier of tubular form into a barrier of rectangular form.

* * * * *